United States Patent [19]

Branner-Jörgensen et al.

[11] 4,357,357
[45] Nov. 2, 1982

[54] THERMAL DESTABILIZATION OF MICROBIAL RENNET

[75] Inventors: Sven Branner-Jörgensen, Charlottenlund; Palle Schneider, Ballerup; Peter Eigtved, Copenhagen, all of Denmark

[73] Assignee: Novo Industri A/S, Denmark

[21] Appl. No.: 96,213

[22] Filed: Nov. 20, 1979

[30] Foreign Application Priority Data

Apr. 9, 1979 [DK] Denmark .............................. 1456/79

[51] Int. Cl.³ ...................... A23C 19/032; C12N 9/58
[52] U.S. Cl. ........................................ 426/36; 426/63; 426/522; 435/223; 435/931
[58] Field of Search ................ 426/36, 63, 330.2, 522; 435/184, 223, 219, 226, 220, 931

[56] References Cited

U.S. PATENT DOCUMENTS

| | | | |
|---|---|---|---|
| 2,053,740 | 9/1936 | Reichert et al. | 426/330.2 |
| 3,275,453 | 9/1966 | Sardinas | 435/223 X |
| 3,886,288 | 5/1975 | Rice et al. | 426/36 |
| 4,086,139 | 4/1978 | Hoerle | 435/184 |

OTHER PUBLICATIONS

Regnier, J. M., Thermal Resistance of Clotting Enzymes, Chem. Abstr., vol. 87:51817a, 1977 (p. 352).
Ilany, et al., Milk–Clotting Activity of Proteolytic Enzymes, J. Da. Sci., vol. 52, No. 1, 1969 (pp. 43–46).

*Primary Examiner*—David M. Naff
*Attorney, Agent, or Firm*—Fidelman, Wolffe & Waldron

[57] ABSTRACT

Microbial rennet such as from *Mucor miehei* is thermally destabilized by treatment of the rennet in an aqueous medium with oxidizing agents containing active chlorine such as hypochlorites. The thermally destabilized rennet is advantageous for cheese making where absence of rennet activity in pasteurized whey is desired.

14 Claims, No Drawings

THERMAL DESTABILIZATION OF MICROBIAL RENNET

This invention relates to a method for thermal destabilization of microbial rennet. Rennet is the designation for a milk coagulating enzyme product.

INTRODUCTION

In the production of cheese, the milk is coagulated in order to be able to separate the curds from the whey. Products containing rennin, which is a milk coagulating enzyme isolated from calf stomach, have long been used for this purpose. In the past, the demand for rennet could be met with calf rennet; but in recent years, several substitutes for calf rennet have been developed, including notably the microbial rennets from *Mucor miehei* and *Mucor pusillus*. *Mucor miehei* rennet is preferred by the cheese art for its low cost, its low unspecific proteolytic activity and its close resemblance to rennin concerning calcium ion sensitivity. The excellent storage stability of *Mucor miehei* rennet is another advantageous property which, at least partly, has been ascribed to its high thermal stability.

Some of the pasteurized whey is utilized as an additive to whole milk, e.g., in the form of a whey powder, to produce enriched milk, for instance as a baby food. The pasteurized whey resulting from cheese made with *Mucor miehei* rennet may still contain a minor level of rennet activity, due to the high thermal stability of the *Mucor miehei* rennet. Any residual rennet activity in the whey powder is undesirable, since protein coagulation is no longer wanted. Such could take place if the whey powder is used for the production of enriched milk as a baby food. The enriched milk may clot before it enters the stomach of the baby, e.g., in the feeding bottle, thereby causing an obstruction to flow of milk out of the bottle.

It is described in *Biochem. Biophys. Acta* 271 (1972) 93-101 (W. S. Rickert, Structural and Functional Determinants of *Mucor miehei* protease, I. Modification of the $NH_2$ terminus and lysine residues by carbamylation) that *Mucor miehei* protease (the active component of *Mucor miehei* rennet) can be carbamylated with potassium cyanate, and that the carbamylated product exhibits a minor degree of thermal destabilization. Practical experiments have shown that the thermal destabilization of the carbamylated enzyme is too small to solve the above-mentioned problem of rennet activity in pasteurized whey. Another approach is in pending application Ser. No. 973,937 filed Dec. 28, 1978, now U.S. Pat. No. 4,255,454, which suggests acylating the enzyme for destabilizing purposes.

The object of this invention is to provide an economically feasible method for thermal destabilization of microbial rennet to such an extent that the disadvantages stemming from the residual microbial rennet activity in pasteurized whey are essentially overcome.

BRIEF STATEMENT OF THE INVENTION

Accordingly, the first aspect of the invention comprises a method for thermal destabilization of microbial rennet, notably the rennet from *Mucor miehei* and *Mucor pusillus* by modification of the microbial rennet through treatment in aqueous solution with oxidizing agents containing active chlorine. Preferred exemplary oxidizing agents are hypochlorites.

DESCRIPTION OF THE INVENTION

It has been found that the microbial rennet modified according to the invention is significantly destabilized and that the degree of destabilization suffices to meet the requirements for whey utilization without having a highly detrimental effect on storage stability of the rennet preparation. Surprisingly it has been found that it is possible, according to the invention, to obtain a destabilization level (as defined hereinafter) of at least 5° C., preferably 7° C.–11° C. which, in the preferred range, makes the thermal stability of the modified enzyme correspond to that of calf rennet whereby the favorable properties of the calf rennet are combined with the favorable properties of the microbial rennet.

The rennet activity is measured according to British Standard 3624: 1963 (Method for the determination of milk coagulating power of rennet).

Since this invention relates to a controlled thermal destabilization of microbial rennet, some elaboration is provided below on techniques to measure thermal stability and to quantify the reduction in thermal stability, i.e., the destabilization, this destabilization being expressed in °C.

Under ideal conditions, an enzyme may be inactivated at a suitable (high) temperature level in such a way that the residual activity of the enzyme decreases as a function of time along an exponential decay curve, i.e., with a well-defined half life, the half life being a function of the temperature (°C.). The half life $T_{\frac{1}{2}}$ can be calculated according to the formula $$T_{\frac{1}{2}} = \frac{(t_2 - t_1)\ln 2}{\ln A_1 - \ln A_2}$$

where $A_1$ is the enzyme activity measured after heating to a specified temperature for the time $t_1$, whereas $A_2$ is the enzyme activity measured after heating to the same specified temperature for the time $t_2$. The half life will be shorter the higher the temperature, everything else being equal. For many enzymes, a change in the pH of the enzyme solution and the ion strength, and the presence of certain salts will influence the half life substantially. Furthermore, chemical derivatization of the enzyme can change the half life considerably. If a chemical derivatization of a particular enzyme causes thermal destabilization of the enzyme, the degree of destabilization is said to be n°C., if the original (non derivatized) enzyme and the derivatized enzyme have the same half life at N°C. and (N−n)°C., respectively.

It should be noted, however, that the destabilization values to a certain degree are approximate, due to the approximative character of the half life value. All destabilization values in this specification are measured at pH 6.0, since the results of the destabilization measurement are pH dependent.

Normally, the treatment according to the invention is accompanied by an activity loss. It has been found that, for economic reasons, the destabilization should not be carried beyond the stage corresponding to an activity loss of around 50%, preferably of around 30%, more preferably less than 10%.

In a typical instance, the destabilization of about 10° C. with an activity loss limited to less than 10% seems to be an appropriate compromise between the above-mentioned conflicting factors.

Examples of oxidizing agents containing active chlorine which can be used in an aqueous reaction mixture according to the invention are hypochlorites, (e.g. sodium hypochlorite), N-chlorosuccinimide, chloramine-T, trichloroisocyanuric acid, and chlorine.

The oxidizing agent should be used in such a concentration that the desired degree of destabilization is obtained in a reasonable time, which may be anything from a few minutes up to 48 hours, or even longer in those instances where the reaction is allowed to proceed unquenched. The ratio of oxidant to total protein in the enzyme product is important to the results. In case the concentration of the oxidizing agent is too small the destabilization will be too small, and in case the concentration of the oxidizing agent is too high the activity loss will be too high. The optimal concentrations ordinarily correspond to a weight proportion between the oxidizing agent and the total amount of protein in the enzyme preparation of about 3 to 30 parts of oxidizing agent per 100 parts of total protein. If the microbial rennet preparation is purified to a high unit activity level the quantity of oxidizing agent may be reduced to as little as 1 gram per 100 grams of total protein.

The pH at which the reaction takes place may vary inside wide limits, i.e. between about pH 3 and 10, with preferred ranges mainly depending upon the oxidizing agent. Thus, with hypochlorite as the oxidizing agent, the preferred pH range is from 5 to 9, and more preferred from 6 to 8.

The reaction temperature is not critical when the reaction temperatures are kept at levels, e.g. below about 30° C., where the stability of the enzyme is satisfactory. However, the stability of the enzyme may be enchanced by addition of known protein stabilizing agents, e.g. NaCl in an amount of 5–20% of the enzyme preparation, or sorbitol in the usual enzyme stabilizing amounts. The preferred reaction temperature range is 0°–30° C.

The underlying reaction mechanisms are not understood, nor is it certain whether the ultimate destabilized enzyme molecule contains any chlorine substituents thereon. Manifestly, the enzyme, like all protein molecules, can and does undergo numerous and diverse reactions, e.g. oxidation and chlorination reactions. Since interest here is in destabilization, any reactions which deactivate the enzyme are undesirable, while those reactions which thermally destabilize the enzyme without reducing enzyme activity are desirable.

The destabilization level of at least 5° C., preferably 7° C. to 11° C., and the accompanying activity loss of no more than 30%, preferably less than 10%, are considered as limits on the practice of this invention. The active chlorine oxidants, including hypochlorite, meet these limits. Free chlorine introduced into an aqueous medium converts to chloride and hypochlorite ions. The N-chloro reagents previously listed convert appropriately to hypochlorite ions. The preferred reagent is sodium hypochlorite, employed at pH 5–9, preferably at pH 6–8.

Acylation as described in copending application Ser. No. 973,937 results in destabilization of about 3° C. Oxidation with hydrogen peroxide also results in destabilization.

Direct treatment of the enzyme with an active chlorine reagent, e.g. sodium hypochlorite, has several process advantages over the peroxide reaction. The principal advantage is believed to be that the active chlorine reagent may be completely consumed in the reaction mixture, while reaction with the peroxide must be terminated, e.g. by addition of catalase.

DETAILED PRACTICE OF THE INVENTION

A preferred embodiment of the method according to the invention comprises the use of a hypochlorite, notably sodium hypochlorite, as the oxidizing agent.

Other preferred embodiments of the method according to the invention comprise use of a reactant selected from the group consisting of chlorine, N-chlorosuccinimide, chloramine-T, and trichloisocyanuric acid.

Another preferred embodiment of the method according to the invention comprises destabilization of *Mucor miehei* rennet.

Another preferred embodiment of the method according to the invention comprises the treatment with from 3 to 30 parts by weight of the oxidizing agent to 100 parts by weight of (total) protein in the enzyme preparation.

The method according to the invention comprises treatment in an aqueous medium at a pH value of between about 3 and 10. With a hypochlorite as the oxidizing agent, the preferred pH range is 5–9, the range of 6–8 being still more preferred.

Another preferred embodiment of the method according to the invention comprises treatment in an aqueous medium at a temperature between 0° C. and 30° C.

As the second aspect, the invention comprises the destabilized microbial rennet prepared by the process of this invention.

As the third aspect, the invention comprises a method for cheese making wherein the rennet according to the present invention is used for milk coagulation. The whey originating from this cheese making process can be used after pasteurization as a protein containing ingredient without any problems.

In practice it has been discovered that the employment of destabilized rennet is preferred for making long-hold cheeses.

The destabilization process may, and preferably is, carried out as the final step in the preparation of the microbial rennet. In fact, (commercially) pure microbial rennet or rennet concentrate may be employed in practice of this invention. Thus, for example, the pH of a microbial rennet solution otherwise ready for the usual finishing operations prior to delivery is adjusted to the predetermined treatment level (e.g. pH 7) and then admixed with stirring at ambient temperature with a solution of the oxidant, the amount of said oxidant being in the afore-mentioned weight proportion range of 3–30 parts (an examplary amount of sodium hypochlorite being 10 parts) per 100 parts of total protein in the microbial rennet solution. The mixture is then left until the desired destabilization level is attained, e.g. for 48 hours. The reaction may be quenched by addition of activated carbon or a reducing agent, such as sodium sulfite, after an appropriate reaction period. The destabilized enzyme product may then be subjected to the usual finishing operations, e.g. filtration, adjustment of pH and unit enzyme activity to standardized levels, etc.

The invention will now be described in more detail by reference to the following examples.

The starting material in the following examples is a rennet concentrate prepared as indicated in "2. Pilot plant experiment" in British Pat. No. 1,108,287, only the culture liquid was concentrated to an activity approximately corresponding to a 1% solution of the pure enzyme (Comptes Rendus des Traveaux du Laboratoire Carlsberg (1970), Vol. 37, No. 14, 301-325) and 18% NaCl was added to the crude concentrate. For the sake of brevity this concentrate will be referred to in the following as "RENNILASE 46."

EXAMPLE 1

Two sets of three 25 ml portions prepared by mixing 12.5 ml of RENNILASE 46 and 12,5 ml of water were adjusted to pH 7.0, 8.0 and 9.0 respectively by addition of 1 N NaOH, and to each of these mixtures was added 0.4 ml of a 2.25 M solution of NaClO, whereby the pH value was kept constant on the above indicated values.

The first set encompassing three portions were placed in a refrigerator (around 18 hours) overnight. The second set encompassing three portions was set aside at room temperature for 2 hours. The pH drop was measured at the end of the periods indicated. Then the portions were diluted by mixing 0.2 ml thereof with 50 ml of water, and simultaneously the pH value was adjusted to 6.0 with sodium acetate/acetic acid.

The pH drops and the residual activities after the reaction between the rennet and the sodium hypochlorite appear from the following table.

|  | pH after | | Residual activity (%) after | |
|---|---|---|---|---|
| Initial pH | 2 hours | 18 hours | 2 hours | 18 hours |
| 7.0 | 6.9 | 6.9 | 86.3 | 83.1 |
| 8.0 | 7.6 | 7.6 | 86.1 | 81.7 |
| 9.0 | 8.2 | 8.2 | 78.4 | 75.4 |

Now the diluted samples were heat treated at 55° C. in 30 minutes at pH 6.0, whereafter the residual activities were measured.

|  | Residual activity (%) after 30 minutes heat treatment at 55° C. | |
|---|---|---|
| Initial pH | 2 hour sample | 18 hour sample |
| 7 | 16.3 | 4.2 |
| 8 | 16.3 | 4.3 |
| 9 | 32.3 | 14.6 |
| Reference |  | 98.7 |

The above indicated residual activities corresponds to the following values of the half life and the destabilization.

|  | $T_{\frac{1}{2}}$, minutes; 30 minutes, 55° C., pH 6.0 | | Destabilization, °C. | |
|---|---|---|---|---|
| Initial pH | 2 hours | 18 hours | 2 hours | 18 hours |
| 7 | 11.5 | 6.5 | 11 | 12 |
| 8 | 11.5 | 6.6 | 11 | 12 |
| 9 | 18.4 | 10.8 | 10 | 11 |
| reference | — | — | — | — |

EXAMPLE 2

The pH of three 150 ml portions of RENNILASE 46 was adjusted to 5.0, 6.0 and 7.0 respectively. Each of these three portions was divided in three parts, to which was added 0.8 ml, 1.2 ml and 1.6 ml of a commercial 2.25 M solution of NaOCl, respectively, whereby pH was kept constant on the above indicated values.

These nine samples were then stored at ambient temperature (22° C.) for 18-20 hours, whereafter a 10 ml sample was taken from each of the nine samples. To each of these 10 ml samples was added 0.4, 0.6 or 0.8 ml 1 M $Na_2SO_3$ solution, respectively, depending upon how much NaOCl was added to the corresponding portion, in order to remove any excess of hypochlorite, if present.

0.2 ml of the thus treated samples were diluted with 50 ml of water, and pH was adjusted to 6.0 with acetic acid/sodium acetate. The diluted and pH adjusted samples were heat treated at 55° C. for 30 minutes. The activity yield, the residual activity after heat treatment and the calculated half life and destabilization appears from the following list.

| pH | Added amount of NaOCl, ml | Activity yield, % | Residual activity, %, 30 minutes, 55° C., pH 6.0 | $T_{\frac{1}{2}}$, minutes, 55° C., pH 6.0 | 30 Destabilization, °C. |
|---|---|---|---|---|---|
|  | 0.8 | 99.4 | 59.4 | 39.9 | 8 |
| 5.0 | 1.2 | 95.3 | 57.6 | 37.7 | 9 |
|  | 1.6 | 84.8 | 56.1 | 36.0 | 9 |
|  | 0.8 | 100 | 53.9 | 33.6 | 9 |
| 6.0 | 1.2 | 91.6 | 50.5 | 30.4 | 9 |
|  | 1.6 | 81.4 | 47.9 | 28.3 | 9 |
|  | 0.8 | 98.1 | 49.1 | 29.2 | 9 |
| 7.0 | 1.2 | 87.7 | 42.7 | 24.4 | 10 |
|  | 1.6 | 78.3 | 35.7 | 20.2 | 10 |

EXAMPLE 3

600 ml of RENNILASE 46 was at a temperature of around 10° C. adjusted to a pH value of 6.0 by means of 4 N NaOH. This portion was divided in six parts of 100 ml each. To each of these six parts was added 0, 0.8, 1.2, 1.6, 2.0 and 2.4 ml respectively of a commercial 2.25 M NaOCl solution, and pH was adjusted to 7 in all six parts.

After around 15 hours at approximately 5° C. 2 ml of 1 M $Na_2SO_3$ was added in order to remove excess of hypochlorite, if any. Addition of sulfite does not change the stability of the rennet. The activity change was measured. Also 5 ml of the samples were diluted 10 times in 0.1 M acetate buffer of pH 6.0, whereafter 5 ml of the diluted samples were heat treated at 60° C. for 15 minutes. The residual activity after heat treatment was determined and the half life and destabilization was calculated. The figures appear from the following table.

| Added amount of 2.25 M NaOCl, ml | Change of total activity, % | % residual activity after heat treatment | $T_{\frac{1}{2}}$, minutes; 15 minutes, 60° C., pH 6.0 | Destabilization, °C. |
|---|---|---|---|---|
| 0 | — | 99 | — | — |
| 0.8 | +0.6 | 35 | 9.9 | 9 |
| 1.2 | 0 | 19 | 6.3 | 10 |
| 1.6 | −4.4 | 14 | 5.3 | 10 |
| 2.0 | −8.5 | 10 | 4.5 | 10 |
| 2.4 | −14.9 | 7 | 3.9 | 11 |

EXAMPLE 4

The starting material in this example was not RENNILASE 46, but RENNILASE 46, to which the addition of 18% NaCl was omitted.

On the basis of the above indicated starting material five 200 g samples were prepared with 0, 5, 10, 15 and 20% NaCl respectively. The pH value was adjusted to 6.0 by means of 4 N NaOH.

From each of the above five 200 g samples a 100 ml sample was taken. To each of the five 100 ml samples was added 1 ml of a commercial 2.25 N NaOCl solution, whereby the temperature was kept between 5° and 10° C. The pH value of all five 100 ml samples was then adjusted to 7.0 with 4 N NaOH and stored at about 5° C.

After a storage time of about 20 hours the activity change was determined. Also 5 ml of the samples were diluted 10 times with 0.1 M acetate buffer of pH 6.0, whereafter 5 ml of the diluted and pH adjusted samples were heat treated at 60° C. for 15 minutes. The residual activity is determined. A not heat treated sample is run parallel as a blank.

The experimental parameters and results appear from the following table.

| Added percentage of NaCl | Added amounts of 2.25 M NaOCl, ml | Change of total activity, % | Residual activity after heat treatment in 15 minutes, % | T½, minutes 15 minutes 60° C., pH 6.0 | Destabilization, °C. |
|---|---|---|---|---|---|
| 0 | 0 | — | 98 | — | — |
| 0 | 1 | −4.2 | 31 | 8.9 | 9 |
| 5 | 1 | +7.8 | 32 | 9.1 | 8 |
| 10 | 1 | +4.0 | 40 | 11.3 | 8 |
| 15 | 1 | +6.8 | 46 | 13.4 | 8 |
| 20 | 1 | +2.4 | 51 | 15.4 | 8 |

EXAMPLE 5

Ten series of experiments were set up at different pH values, viz. 2.5, 3.0, 4.0, 5.0, 6.0, 7.0, 8.0, 9.0, 10.0 and 11.0. Each series consisted of 3 samples, prepared by diluting aliquots of 12.5 ml of RENNILASE 46 with an equal volume of water. To the first sample of each series was added 75 μl of a commercial 2.25 M solution of sodium hypochlorite, to the second 150 μl and to the third 300 μl, which amounts correspond to (approximately) 4, 8 and 16 grams, respectively, of sodium hypochlorite per 100 grams of total protein of the sample. The pH of each series was kept constant at the indicated values. The reaction temperature was the same for all series (approximately 5° C.).

After reaction times of approximately 114, 66 and 90 hours for the first, second and third sample, respectively, of each series, all samples were made up to 50 ml. Samples for analysis were prepared by suitable dilution (approximately 1:125), pH at the same time being adjusted to 6.00 by means of acetic acid and sodium acetate solutions.

These samples were then heat treated at 55° C. for 30 minutes. Activity yield, residual activity after heat treatment, the calculated half life and destabilization calculated therefrom are presented in the following table.

| Initial pH | Amount of NaClO add. μl/25 ml sample | Terminal pH | Activity yield, % | Residual activity, % | T½ min. | Destabilization, °C. |
|---|---|---|---|---|---|---|
| 2,5 | 75 | 2,52 | 93,0 | 77,3 | 80,8 | 6 |
| | 150 | 2,75 | 80,5 | 71,6 | 62,2 | 7 |
| | 300 | 2,50 | 16,2 | 40,7 | 23,1 | 9 |
| 3 | 75 | 3,00 | 101,3 | 76,9 | 79,2 | 6 |
| | 150 | 3,15 | 97,6 | 60,5 | 41,4 | 8 |
| | 300 | 3,00 | 32,4 | 70,0 | 22,7 | 9 |
| 4 | 75 | 3,96 | 106,1 | 71,8 | 62,8 | 7 |
| | 150 | 4,05 | 102,4 | 64,2 | 46,9 | 8 |
| | 300 | 3,94 | 69,8 | 41,3 | 23,5 | 9 |
| 5 | 75 | 4,95 | 104,4 | 74,5 | 70,6 | 7 |
| | 150 | 4,99 | 99,4 | 62,2 | 43,8 | 8 |
| | 300 | 4,80 | 71,1 | 45,1 | 26,1 | 10 |
| 6 | 75 | 5,86 | 101,7 | 59,4 | 39,9 | 8 |
| | 150 | 5,98 | 94,8 | 40,8 | 23,2 | 9 |
| | 300 | 5,66 | 61,5 | 8,6 | 8,48 | 11 |
| 7 | 75 | 6,61 | 96,3 | 39,5 | 22,4 | 9 |
| | 150 | 6,64 | 90,2 | 7,1 | 7,86 | 11 |
| | 300 | 6,51 | 49,2 | 4,0 | 6,46 | 11 |
| 8 | 75 | 7,40 | 94,3 | 48,3 | 28,6 | 8 |
| | 150 | 7,26 | 87,1 | 6,4 | 7,57 | 11 |
| | 300 | — | — | — | — | — |
| 9 | 75 | 8,02 | 90,4 | 68,2 | 54,3 | 7 |
| | 150 | 7,79 | 77,7 | 17,5 | 11,9 | 10 |
| | 300 | 7,34 | 47,3 | 9,3* | 2,92* | 13 |
| 10 | 75 | 8,34 | 81,2 | 78,6 | 86,4 | 6 |
| | 150 | 8,23 | 68,5 | 34,0 | 19,3 | 9 |
| | 300 | 7,83 | 44,4 | 9,3* | 2,92* | 13 |
| 11 | 75 | 10,34 | 57,2 | 93,5 | 30,9 | 4 |
| | 150 | 10,02 | 42,2 | 74,4 | 70,3 | 7 |
| | 300 | 9,80 | 9,9 | — | — | |

*10 min. heat treatment.

These data indicate the following conditions to be optimal for destabilization with sodium hypochlorite: pH range: 6–8.

Amount of sodium hypochlorite: 150 μl of 2.55 M solution per sample, corresponding to (approximately) 8 g of sodium hypochlorite per 100 g of total protein.

EXAMPLE 6

Two portions were prepared of a mixture of 25 ml RENNILASE 46 and 20 g ice water, wherein pH was adjusted to 7.0 by means of 4 N NaOH.

To these two portions was added 33 and 66 mg of N-chlorosuccinimide, respectively, dissolved in 5 ml of ice water, whereby pH simultaneously was adjusted to 7.0.

Two hours later 0.2 ml of the portions were diluted with 50 ml of water, whereby pH simultaneously was adjusted to 6.0 by means of sodium acetate/acetic acid.

The residual activity after the reaction between the rennet and the N-chlorosuccinimide were the following:

| Added amount of N-chlorosuccinimide, mg | Residual activity, % |
|---|---|
| 33 | 99.0 |
| 66 | 96.5 |

In the same manner as in example 1 heat treatment was carried out at 55° C. in 30 minutes at pH 6.0. Thereafter the residual activities were determined and the half lives and destabilizations calculated. The results appear from the following table.

| Added amount of N—chlorosuccinimide mg | Residual activity, 55° C. in 30 minutes, pH 6.00, % | T½, minutes; 30, minutes, 55° C., pH 6.0 | Destabilization, °C. |
|---|---|---|---|
| 33 | 41.5 | 23.6 | 10 |

-continued

| Added amount of N—chlorosuccinimide mg | Residual activity, 55° C. in 30 minutes, pH 6.00, % | T½, minutes; 30, minutes, 55° C., pH 6.0 | Destabilization, °C. |
|---|---|---|---|
| 66 | 26.4 | 15.6 | 10 |

EXAMPLE 7

50 ml of RENNILASE 46 was diluted with 50 ml of water. The mixture was cooled in an ice bath, and pH was adjusted to 7.0 with 1 N NaOH. Then around 0.1 g of free $Cl_2$ was introduced; thereby pH dropped to around 3.8, and the liquid turned turbid and brighter. The reaction mixture was left for around 10 minutes, and then 4 ml 1 M $Na_2SO_3$ solution was added in order to remove excess of $Cl_2$.

0.2 ml samples before and after $Cl_2$ addition were diluted with 50 ml of water, and pH was adjusted to 6.0 with sodium acetate/acetic acid. the activity loss associated with the reaction between rennet and chlorine was 21%.

After the heat treatment of the chlorine treated rennet at 55° C. in 30 minutes a residual activity of 63% was found. This corresponds to a half life of around 45 minutes or a destabilization of about 8° C.

EXAMPLE 8

Two portions were prepared of 25 ml of RENNILASE 46 and 25 g of ice water, and pH was adjusted to 7.0 with 4 N NaOH.

To these two mixtures were added 60 and 120 mg trichloroisocyanuric acid, respectively, and simultaneously the pH was adjusted to 7.0.

Approximately 4 hours later 0.2 ml of the above mixtures were diluted with 50 ml of water, and simultaneously pH was adjusted to 6.0 with sodium acetate/acetic acid. The thus diluted samples were heat treated at 55° C. for 30 minutes.

The activity yields, the residual activities after heat treatment and the calculated half lives and destabilizations appear from the following list.

| Amount of added trichloroisocyanuric acid, mg | Activity yield, % | T½, minutes; 30 minutes, 55° C. pH 6.0 | Destabilization, °C., |
|---|---|---|---|
| 60 | 93.0 | 35 | 9 |
| 120 | 81.5 | 16 | 10 |

EXAMPLE 9

Two portions of 25 ml of RENNILASE 46 were mixed with 20 g of ice water for each portion, and pH was adjusted to 7.0 with 4 N NaOH.

Then 70 and 140 mg, respectively, of chloramin-T, dissolved in 5 ml ice water, was added to the two above portions, and simultaneously pH was adjusted to 7.0.

Approximately two hours later 0.2 ml of the above samples were diluted with 50 ml of water, pH being simultanously adjusted to 6.0 with sodium acetate/acetic acid, and the thus diluted and pH adjusted samples were heat treated at 55° C. for 30 minutes. Activity yields, residual activities after heat treatment and calculated values of half life and destabilization appear from the below given list.

| Amount of added chloramin T - mg | Activity yield, % | T½, minutes, 30 minutes; 55° C., pH 6.0 | Destabilization, °C. |
|---|---|---|---|
| 70 | 96.5 | 19.2 | 10 |
| 140 | 77.9 | 8.5 | 12 |

EXAMPLE 10

3 g of *Mucor pusillus* protease (Noury, 1: 220.000) is dissolved in 30 ml 10% NaCl, and the pH value is adjusted to 6.5 at 5°–10° C. 3×50 µl 15% NaOCl are added at intervals of 30 minutes. After stirring for 3 hours the mixture is kept at 4° C. for 16 hours, and the pH value is then adjusted to 5.0. Samples are collected for the determination of activity and thermostability. The results appear from the table below.

| Sample/reaction time | Activity yield % | Half life at pH 6.0, 0–30 minutes at: (min.) | | Destabilization (°C.) |
|---|---|---|---|---|
| | | 50° C. | 55° C. | |
| Reference | 100 | 144–155 | 18–31 | — |
| 24 hours | 84–91 | 26–22 | 5–11 | 5 |

What we claim is:

1. A method for producing microbial rennet having reduced thermal stability for use in cheese making comprising reacting Mucor microbial rennet in an aqueous medium with an oxidizing agent containing active chlorine to produce a microbial rennet having a reduced thermal stability of at least 5° C. and having at least about 50% of the rennet activity before said reaction.

2. The method of claim 1 wherein the oxidizing agent is selected from the group consisting of hypochlorite, N-chlorosuccinimide, chloramin-T, trichloroisocyanuric acid, and chlorine.

3. The method of claim 1 wherein the oxidation is conducted in the presence of an enzyme stabilizing agent.

4. The method of claim 1 wherein the microbial rennet is *Mucor miehei* rennet.

5. The method of claim 1 wherein the aqueous medium has a pH value of between 3 and 10.

6. The method of claim 1 wherein the aqueous medium has a temperature of between 0° C. and 30° C.

7. The method of claim 1 wherein the oxidizing agent is sodium hypochlorite.

8. The method of claim 7 wherein the rennet activity loss is not more than about 10%.

9. The method of claim 7 wherein the treatment is conducted with a weight proportion of from 3 to 30 parts of oxidizing agent per 100 parts of total protein in the microbial rennet.

10. The method of claim 7 wherein the aqueous medium has a pH value of between 5 and 9.

11. A thermally destabilized microbial rennet prepared by the process of claim 1.

12. A method for making cheese comprising coagulating milk with Mucor microbial rennet modified by the process of claim 1 to produce cheese and whey, pasteurizing the whey and using the whey to produce human food.

13. A method for producing microbial rennet having reduced thermal stability for use in cheese making comprising reacting *Mucor miehei* microbial rennet in an aqueous medium with a modifying agent selected from the group consisting of hypochlorite and trichloroisocyanuric acid to produce a microbial rennet which has reduced thermal stability and which retains a major part of its milk coagulating activity.

14. A method for making cheese comprising coagulating milk with *Mucor miehei* microbial rennet produced by the process of claim 13 to produce cheese and whey, pasteurizing the whey and using the whey to produce human food.

* * * * *